United States Patent
Barthel (10) Patent No.: US 9,623,214 B2
(45) Date of Patent: *Apr. 18, 2017

(54) METHOD OF DILATING GASTROINTESTINAL STRICTURES USING A TRANS-ENDOSCOPIC HYDRAULIC BALLOON APPARATUS

(71) Applicant: James Stephen Barthel, Tampa, FL (US)

(72) Inventor: James Stephen Barthel, Tampa, FL (US)

(73) Assignee: University of South Florida, Tampa, FL (US)

( * ) Notice: Subject to any disclaimer, the term of this patent is extended or adjusted under 35 U.S.C. 154(b) by 43 days.

This patent is subject to a terminal disclaimer.

(21) Appl. No.: 14/819,000

(22) Filed: Aug. 5, 2015

(65) Prior Publication Data

US 2015/0367114 A1 Dec. 24, 2015

Related U.S. Application Data

(63) Continuation of application No. 12/791,180, filed on Jun. 1, 2010, now Pat. No. 9,126,024, which is a
(Continued)

(51) Int. Cl.
  *A61M 29/02* (2006.01)
  *A61M 25/10* (2013.01)
  (Continued)

(52) U.S. Cl.
  CPC .. *A61M 25/10184* (2013.11); *A61M 25/1002* (2013.01); *A61M 25/1018* (2013.01);
  (Continued)

(58) Field of Classification Search
  CPC ........ A61M 25/1018; A61M 25/10181; A61M 25/10182; A61M 5/48; A61M 5/484;
  (Continued)

(56) References Cited

U.S. PATENT DOCUMENTS

| | | | | |
|---|---|---|---|---|
| 4,583,974 A | * | 4/1986 | Kokernak | A61M 25/10182 604/211 |
| 4,826,483 A | * | 5/1989 | Molnar, IV | A61M 5/5013 604/110 |
| 2004/0122361 A1 | * | 6/2004 | Hart | A61M 25/10184 604/97.02 |

* cited by examiner

*Primary Examiner* — Katherine Rodjom
(74) *Attorney, Agent, or Firm* — Michele L. Lawson; Smith & Hopen, P.A.

(57) ABSTRACT

A trans-endoscopic hydraulic balloon dilation apparatus includes a fluid reservoir containing a hydraulic fluid. A shaft has a lumen in fluid communication with a leading end of the fluid reservoir. A balloon is mounted on the shaft and an opening in the shaft enables hydraulic fluid to flow through the opening into or from the balloon. A piston secured to a leading end of a piston rod is slideably positioned within a lumen of the fluid reservoir. A hub secured to a trailing end of the fluid reservoir is centrally apertured to accommodate the piston rod so that a trailing end of the piston rod is external to the fluid reservoir. Displacement of the piston rod in a trailing-to-leading direction causes expansion of the balloon. Displacement of the piston rod in a leading-to-trailing direction causes deflation of the balloon. The piston can be locked into any position.

12 Claims, 4 Drawing Sheets

Related U.S. Application Data continuation of application No. PCT/US2008/085124, filed on Dec. 1, 2008.

(60) Provisional application No. 60/991,415, filed on Nov. 30, 2007.

(51) Int. Cl.
*A61B 17/02* (2006.01)
*A61B 17/32* (2006.01)

(52) U.S. Cl.
CPC ......... *A61M 29/02* (2013.01); *A61B 17/0218* (2013.01); *A61B 2017/320048* (2013.01); *A61M 2029/025* (2013.01); *A61M 2210/1042* (2013.01)

(58) Field of Classification Search
CPC ...... A61M 5/486; A61M 5/488; A61M 5/178; A61M 5/31511; A61M 5/31526; A61M 5/5013
See application file for complete search history.

# METHOD OF DILATING GASTROINTESTINAL STRICTURES USING A TRANS-ENDOSCOPIC HYDRAULIC BALLOON APPARATUS

CROSS REFERENCE TO RELATED APPLICATIONS

This application is a continuation of and claims priority to U.S. patent application Ser. No. 12/791,180, entitled "Trand-Endoscopic Hydraulic Balloon Apparatus", filed Jun. 1, 2010, which is a continuation of and claims priority to International Application, Serial Number PCT/US2008/085124 filed Dec. 1, 2008, which claims priority to U.S. Provisional Patent Application No. 60/991,415, filed Nov. 30, 2007, the contents of each of which is hereby incorporated by reference into this disclosure.

BACKGROUND OF THE INVENTION

Trans-endoscopic balloon dilation of accessible gastrointestinal tract strictures offers the advantage of not requiring removal of the endoscope and insertion of a different device (frequently under fluoroscopic guidance) in order to accomplish dilation. Procedure durations are therefore minimized, patient and staff exposure to radiation is avoided, and, when the procedure is to be continued beyond the dilation, the necessity of repeating endoscopic insertion is eliminated. The later is particularly important in minimizing risk to the patient in those instances where initial passage of the endoscope to the location of the stricture is difficult.

Through the endoscope, balloon dilation of tight esophageal strictures is frequently carried out with fluoroscopic monitoring. A stricture is considered to be "tight" if an endoscope cannot be passed through it. Fluoroscopic monitoring of tight stricture dilation is believed to help prevent sudden fracture or splitting of the stricture and thus reduce the risk of esophageal perforation during the dilation procedure. Currently available dilation balloons are made of transparent material to facilitate visualization. U.S. Pat. No. 6,953,431 to Barthel, which is incorporated herein by reference, discloses an apparatus that enables direct observation of the stricture wall response during balloon dilation. This is an advantage unique to balloon dilation that is not possible with other dilation techniques.

Examination and accurate measurement of an esophageal stricture can only be accomplished visually or endosonographically if the endoscope can be passed completely through the stricture. Two techniques exist for accomplishing complete stricture passage with balloon dilation. The traditional method is to pass and inflate successively larger balloons across the stricture until a diameter of 15 to 40 mm is achieved. The last dilation balloon is then removed and the instrument is maneuvered through the stricture under direct unguided operator control. The post-dilation 15 or 40 mm diameter stricture lumen is 5 or 6 mm larger than the diameter of a standard video endoscope and 2 to 3 mm larger than the diameter of an echoendoscope. However, stricture elasticity, luminal tortuosity, and frequent shelving (stepped areas along the stricture) can prevent passage of the instrument, despite an apparently adequate dilation.

An alternative method for accomplishing complete stricture passage with balloon dilation is the "balloon-scope train method." The stricture is dilated to a diameter 1 or 2 mm larger than the diameter of the endoscope. The endoscope is then pushed up against the proximal end of the inflated dilation balloon to form a balloon-scope "train." The combination of balloon and endoscope is then advanced through the stricture.

Conventional trans-endoscopic balloon dilation systems, however, require a level of mechanical understanding and operational training that is seldom available among the individuals called upon to assemble and operate the devices during endoscopic procedures. More specifically, the components that must be collected and assembled include a shaft mounted balloon, an inflation gun, a manometer, and saline or other suitable fluid. The collection of these components and their assembly is required to render the currently available balloon dilation systems operational. The resulting procedural delays and device operation errors arising from improper assembly significantly mitigate the advantages of trans-endoscopic balloon dilation.

Thus, there is a need for a trans-endoscopic balloon dilation system that does not require intra-procedure assembly of components and the delays and errors that result therefrom. The needed device would be fully assembled in a factory and it would be pre-filled with a suitable fluid for balloon dilation. Such a device would enable an operating team to concentrate on the surgical procedure without the distraction of assembling a tool and the problems and delays associated with such assembly.

SUMMARY OF INVENTION

An endoscopic dilation instrument assembly comprises, in accordance with the present invention, a hydraulic fluid reservoir in fluid communication with a balloon having at least one expandable or inflatable end portion. An elongate hollow shaft is provided for connecting the balloon to the fluid reservoir, with the balloon being disposed in a collapsed configuration along an outer surface of the shaft. An inflation element within the fluid reservoir is operatively coupled with the balloon for enabling the inflation of the balloon from the collapsed configuration to an expanded use configuration in which the inflation element pushes the hydraulic fluid in a distal direction away from the trailing end of the reservoir for spreading internal tissues of a patient to facilitate access and/or viewing of the tissues. Deflation of the balloon from the expanded use configuration to the collapsed configuration is provided in which the inflation element draws the hydraulic fluid in a proximal direction away from the balloon.

Pursuant to another feature of the present invention, the inflation element comprises a piston, secured to a leading end of an elongate piston rod, slideably positioned within a lumen of the fluid reservoir. A hub is secured to a trailing end of the fluid reservoir. The hub is centrally apertured to accommodate the piston rod so that a trailing end of the piston rod is external to the fluid reservoir. A piston rod handle is mounted to the trailing end of the piston rod. Displacement of the handle and hence the piston in a trailing-to-leading (proximal-to-distal) direction therefore causes expansion of the balloon. Displacement of the handle and hence the piston in a leading-to-trailing (leading-to-trailing) direction causes deflation of the balloon.

In a preferred embodiment, the inflation element includes a locking mechanism for securing the inflation mechanism, and the diameter of the balloon by extension, in a preselected position. Although the locking means may take many forms, in a preferred embodiment the locking means includes a plurality of ratchet members formed in the piston rod along an extent thereof. The ratchet members of this preferred embodiment engage a ratchet plate disposed within the hub. Each of the plurality of ratchet members engage the periphery of an elongate opening formed in the ratchet plate as the piston is displaced in a trailing-to-leading direction.

Another feature of the invention includes graduation markings provided on the transparent or substantially transparent, translucent fluid reservoir. The movement of the piston relative to these markings corresponds to a predetermined volume of hydraulic fluid being expelled from, or drawn into, the fluid reservoir. Accordingly, the user may position the piston in alignment with said markings to ascertain the diameter of the balloon based on the amount of fluid therein and does not require direct visualization thereof. Optionally, the spacing of the graduated markings corresponds to the spacing of the ratchet members. The graduated markings can represent the volume of fluid within the fluid reservoir or can represent the diameter of the balloon.

Furthermore, the long-standing but heretofore unfulfilled need for a pre-assembled and pre-filled trans-endoscopic balloon dilation system is now met by a yet another embodiment of the invention. The inventive structure of this embodiment is an integrally formed, single-unit trans-endoscopic self-contained, pre-filled hydraulic balloon dilation apparatus that requires no assembly by the end user.

BRIEF DESCRIPTION OF THE DRAWINGS

For a fuller understanding of the invention, reference should be made to the following detailed description, taken in connection with the accompanying drawings, in which.

DETAILED DESCRIPTION OF THE PREFERRED EMBODIMENT

In the following detailed description of the preferred embodiments, reference is made to the accompanying drawings, which form a part hereof, and within which are shown by way of illustration specific embodiments by which the invention may be practiced. It is to be understood that other embodiments may be utilized and structural changes may be made without departing from the scope of the invention.

Figure 1:
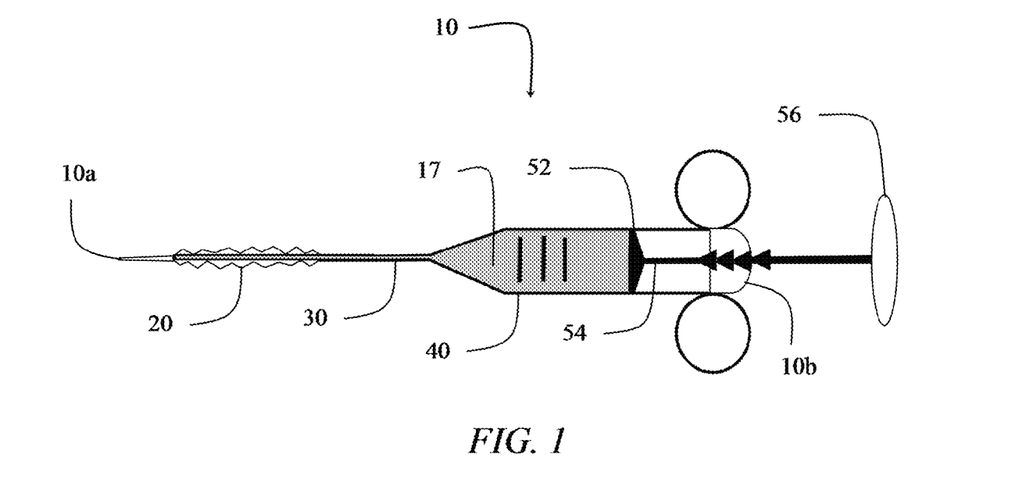
FIG. 1 is a diagrammatic, side elevational view of the novel endoscope when the balloon is deflated.
Figure 2:
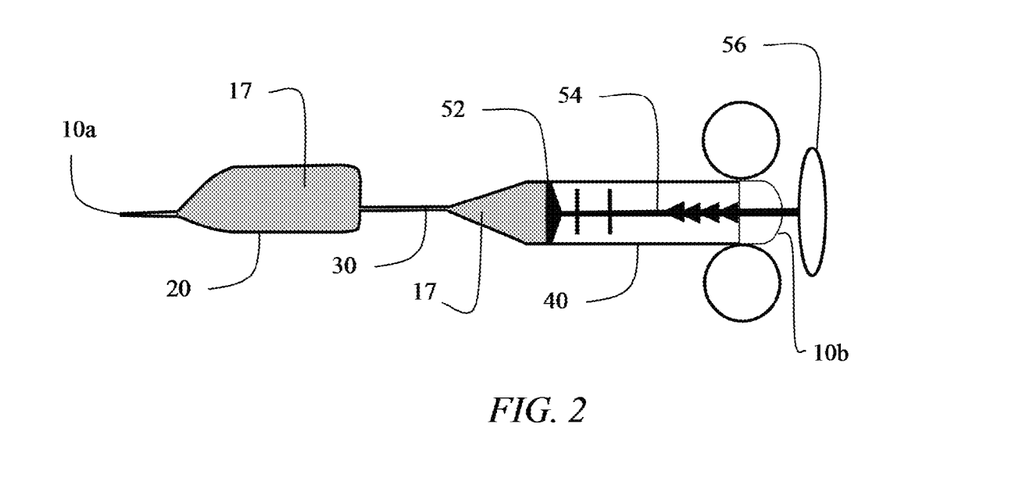
FIG. 2 is a diagrammatic, side elevational view of the novel endoscope when the balloon is inflated.

The present invention includes embodiments of a endoscopic dilation device 10, such as that depicted in FIGS. 1 and 2, configured to facilitate negotiation of the scope through a stricture or other difficult or tortuous pathway within the body, and/or to abut the viewing port or objective lens of an endoscope face such that anatomical structures of interest can be viewed.

Referring now to FIGS. 1 through 3C, it will be seen that an illustrative embodiment of endoscopic dilation device is denoted as a whole by the reference numeral 10 and has leading end 10a and trailing end 10b. Balloon 20, typically made of a clear, non-distensible polymer material such as transparent polyethylene terephthalate (PET), is mounted on shaft 30, made of a flexible catheter material, near the leading end (30a, FIG. 3A) thereof and is depicted in a deflated configuration in FIG. 1 and in an inflated configuration in FIG. 2. Trailing end 30b of shaft 30 is in fluid communication with fluid reservoir 40 having a conical leading end 40a and a cylindrical trailing end 40b defined by transparent or translucent barrel 42. Fluid reservoir 40 houses hydraulic fluid 17, such as water or saline. Leading end 10a generally provides an atraumatic means of cannulating a stricture or generally guiding the balloon through a passageway.

Figure 3A:
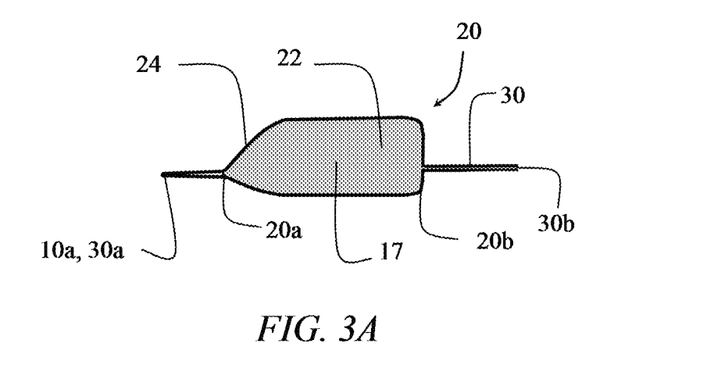
FIG. 3A is a diagrammatic, side-elevation detail of the shaft and balloon wherein the balloon is inflated.
Figure 3B:
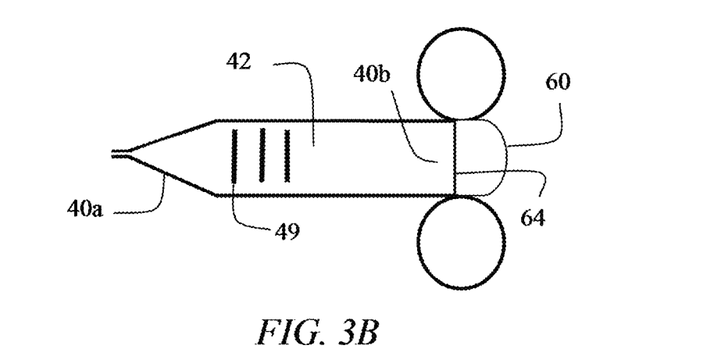
FIG. 3B is a diagrammatic, side-elevation detail of the fluid reservoir and hub.

The illustrative balloon 20, depicted in greater detail in FIG. 3A, comprises a main portion 22 that is generally uniformly cylindrical in shape, and a tapered portion 24 toward the leading end 20a of the balloon portion 20. The trailing end 20b of balloon 20 is generally truncate in shape such that the trailing end 20b can be cinched or drawn against the distal face of an endoscope (not shown) from which it has been advanced, such that there is a broad area of contact between the balloon and at least a substantial cross section of the endoscope face. The area of contact includes the viewing port or objective lens (not shown), and preferably, but not essentially, the light source (not shown) such that the balloon portion generally serves as an extension of the lens, thereby enabling the endoscopist a relatively unobstructed and undistorted view through the balloon interior, which permits visualization of the anatomical structures within the body conduit.

The main portion 22 of balloon 20 includes a central axis that intersects the cross-sectional center point of the main cylindrical portion 22. Balloon 20 also includes a luminal axis that intersects the leading and trailing openings thereof. In a preferred embodiment, the luminal axis of the present invention comprises the original lumen of the tubing used to form balloon 20, but unlike a standard dilation balloon, is offset relative to the central axis to allow alignment with the endoscope. Generally, it is desired that balloon 20 and outer contours of the endoscope be concentrically aligned with one another to maximize the field of view and reduce ledges or surfaces that are prone to catch upon a shelf or stricture during advancement of the balloon-scope train.

Although having the balloon diameter closely match that of the endoscope provides the ideal clinical situation for introduction of the balloon-scope train, it is not necessary to the invention that the balloon and scope be of the same diameter. Often, multiple sizes of balloons are used with a given endoscope for a single procedure, such as in esophageal dilation procedures, where attempting to fully dilate in a single, rather than multiple stages, increases the risk of rupture. The standard sizes of endoscopes used in gastrointestinal procedures are 8.5, 9.5 and 11.5 mm, which are generally compatible with the most preferred range of balloon diameters for the illustrative embodiment (10-40 mm).

Balloon 20 of the illustrative embodiment of FIGS. 1 and 2 is formed by a well-known means, such as blow molding, whereby a length of PTE tubing, sufficient in length to form the final desired length of the balloon, is placed and clamped within a mold conforming to the final shape of the fully distended balloon. Hot air is passed through the tubing, causing the tubing to expand against the contours of the mold. The tubing and molding process parameters necessary to achieve the desired balloon are determined by the required burst strength and recommended pressure of the balloon, the material used, and the size of the balloon. One source of balloon 20 of the illustrative embodiment is Advanced Polymers, Inc. (Salem, N.H.). The typical range of diameters for an 8 cm long esophageal dilation balloon is generally about 6 to 19 mm, with a more preferred range of 12-18 mm. Minimum specified burst pressures typically average 175 psi for a 12 mm balloon, down to about 122 mm for an 18 mm diameter balloon, with the corresponding recommended pressures being about 90 and 50 psi, respectively. Pyloric and colonic dilation balloons are typically shorter in length (e.g., 5.5 cm); however, the recommended pressures are generally the same as the longer esophageal balloons for corresponding diameters.

In certain embodiments, the proximal end of the balloon is indented. Such indentations can permit the endoscopist to lock or otherwise more completely engage the proximal end of the balloon with the distal end of the endoscope, thereby resisting rotational movement and thus minimizing rotational loss of balloon/scope alignment. One such exemplary embodiment comprises an indentation which effectively results in a circumferential flange at the proximal end of the balloon that is configured to frictionally engage the distal end of the endoscope.

In the illustrative embodiment of FIGS. 1 and 2, shaft 30 includes a single lumen that provides an infusion pathway to balloon 20, whereby water or saline is introduced, via reservoir 40. The balloon is maintained in a deflated state and is folded and inserted into a delivery sheath (not shown). It is then advanced from the delivery sheath into the instrument (accessory) channel of the endoscope, which typically is a minimum of 2.8 mm for an illustrative esophageal dilation balloon, as well as the related pyloric, or colonic embodiments in which the balloon is 18 mm or smaller in diameter when inflated. Examples of other clinical applications include, but are not limited to, biliary tree, bronchial tree, neural endoscopy and the vascular system. Larger diameter balloons, e.g., 19-20 mm, may require an instrument channel of up 3.7 mm or greater. Typically, the balloon is lubricated to ease insertion into the endoscope instrument channel. Shaft 30 of the illustrative embodiment and related embodiments has an outer diameter of approximately 0.085" and an inner diameter of approximately 0.058". The esophageal and colonic embodiments typically have an overall length, including balloon, of approximately 420 cm, although any length that is appropriate for a particular endoscope may be used. A colonic dilation balloon catheter, for example, is typically longer, e.g., 240 cm.

Figure 3C:
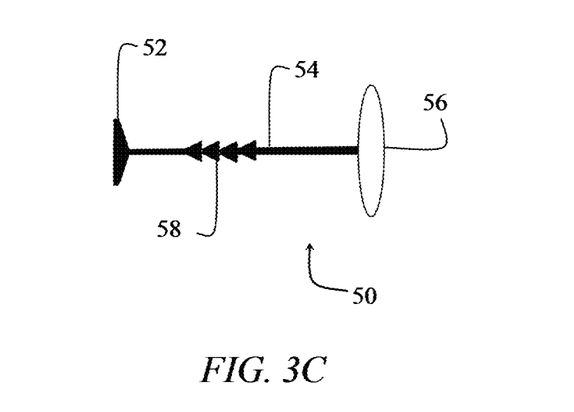
FIG. 3C is a diagrammatic, side-elevation detail of the inflation element.

Piston 52 is slideably positioned within the lumen of barrel 42 and said piston is secured to the distal end of elongate piston rod 54 to form inflation element 50 (FIG. 3C). Barrel 42 is transparent or translucent so that the instantaneous position of piston 52 within said barrel is observable by the user. Piston rod handle 56 is secured to the trailing end of piston rod 54. Piston rod handle 56 facilitates force transfer to hydraulic fluid 17.

In a preferred embodiment, inflation element 50 includes a locking mechanism for securing the inflation mechanism, and the diameter of the balloon by extension, in a preselected position. Although there are numerous ways to lock inflation element 50 within a cylinder in multiple positions of functional adjustment, a simple ratchet system is preferred. The invention is not restricted to any particular locking means, however, and alternate mechanisms will be apparent to the skilled artisan without departing from the contemplated invention.

In this illustrative embodiment, a plurality of ratchets, having an arrowhead or wedge shape, collectively denoted 58, is formed along a predetermined extent of piston rod 54. Each ratchet is narrow at its leading end and wide at its trailing end to facilitate proximal-to-distal displacement of piston 52 and to substantially prevent inadvertent leading-to-trailing displacement. Only one (1) of said ratchets 58 is internal to fluid reservoir 40 in FIG. 1 when handle 56 is in a retracted position. Four (4) of said ratchets are internal to fluid reservoir 40 in FIG. 2 when said handle is in an extended position. Balloon 20 is inflated in FIG. 2 because piston rod handle 56 has been displaced in a trailing-to-leading direction relative to its FIG. 1 position.

Figure 4A:
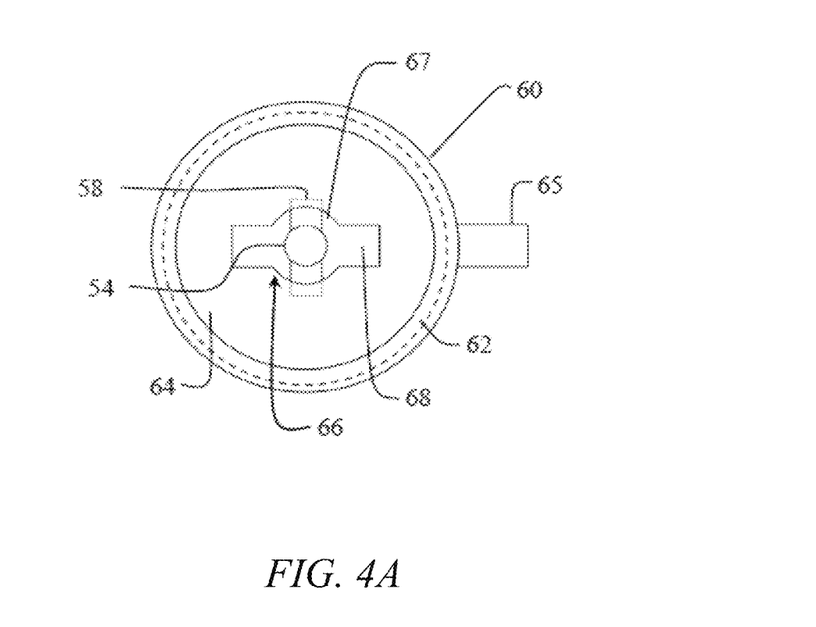
FIG. 4A is a diagrammatic, end elevation view of a ratchet lock and release device wherein the ratchet plate is engaged with the trailing end of the piston, thereby locking the inflation element in a preselected position.
Figure 4B:
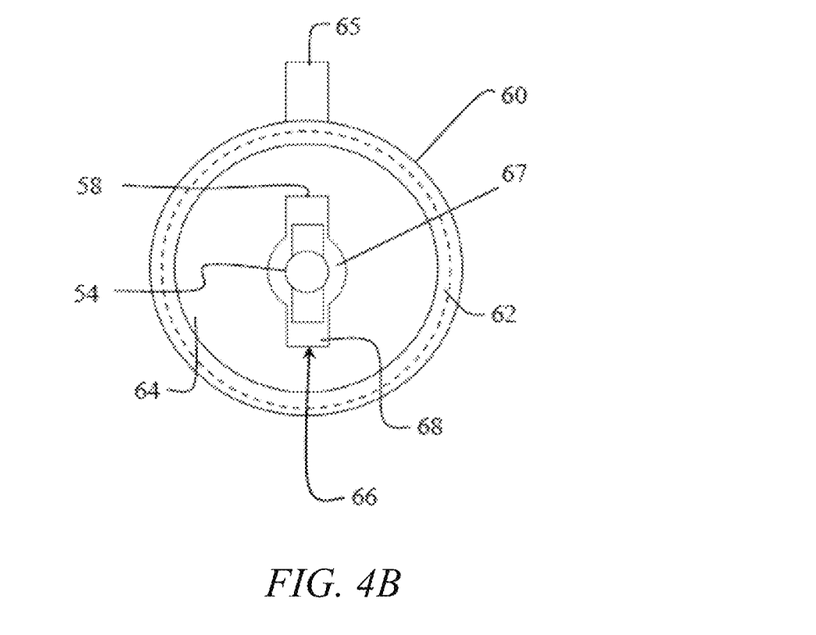
FIG. 4B is a diagrammatic, end elevation view of a ratchet lock and release device wherein the ratchet plate is rotated to disengage the trailing end of the piston, thereby allowing the inflation element to be retracted.

Hub 60 is secured or integrally formed with the proximal or trailing end of barrel 42. As depicted in FIGS. 4A and 4B, said hub has an annular recessed step 62 formed therein. Disc-shaped ratchet plate 64 has a thickness substantially equal to a depth of step 62 so that said plate 64 is substantially flush with the hub. An annular peripheral edge of ratchet plate 64 is supported by the tread of step 62.

Ratchet plate handle 65 is formed integrally with ratchet plate 34 and extends radially therefrom. Hub 60 has a cutout section formed in its annular peripheral edge that extends about ninety degrees (90°) to allow rotation of ratchet plate handle 65 about the longitudinal axis of symmetry of device 10.

An elongate opening or ratchet slit 66 is formed in ratchet plate 64 in registration with a diameter thereof. Slit 66 is enlarged at its mid-point 67 to accommodate piston rod 54. However, enlarged opening 67 has a width less than a breadth of each ratchet 58. Accordingly, when the assembly is in the configuration depicted in FIG. 4A, advancing piston rod 54 causes each ratchet 58 to momentarily compress as it is forced to pass through said opening 67. The resilience of each ratchet 58 causes it to return to its uncompressed position of repose after it has passed through said opening 67, as indicated by the depiction of ratchet 58 in FIG. 4A. Due to the wedge or arrowhead shape of the ratchets, they cannot travel through opening 67 in a leading-to-trailing direction when in the FIG. 4A position. Accordingly, when there is at least one (1) ratchet on the leading or distal side of opening 67, and at least one (1) ratchet on the trailing or proximal side of said opening, then piston 52 is locked into position. The ability to lock the piston into a plurality of positions of functional adjustment enables controlled balloon dilation.

The resistance to movement offered by ratchets 58 in a proximal-to-distal direction is not great so a user may overcome said resistance by pushing on piston rod handle 56. A clicking sound is heard as each ratchet momentarily compresses and pops back into its position of repose upon passing through opening 67, and the user may also feel each ratchet passing through said opening. The user observes the position of piston 52 relative to markings 49 to ascertain the volume of fluid dispensed into balloon 20. Determination of balloon expansion (A balloon radius) by volume transfer markings 49 provides a more accurate measurement than the prior art technique of monitoring system pressure with a manometry gauge.

When retraction of piston 52 and hence deflation of balloon 20 is desired, the user may rotate ratchet plate handle 65 to align ratchets 58 with elongate opening 68 formed in ratchet plate 64, FIG. 4B. Ratchets 58 may then be withdrawn through said elongate opening in a leading-to-trailing direction.

Figure 5A:
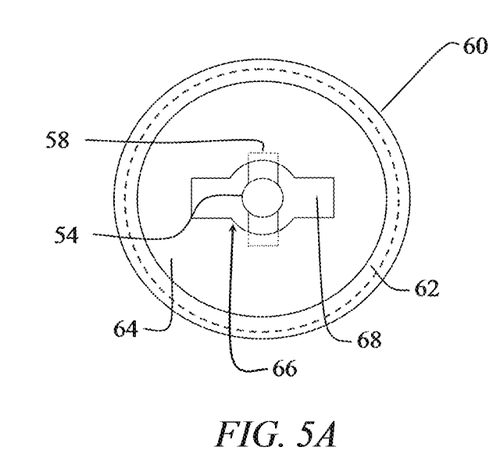
FIG. 5A is a diagrammatic, end elevation view of a ratchet lock and release device wherein the ratchet plate is engaged with the trailing end of the piston, thereby locking the inflation element in a preselected position.
Figure 5B:
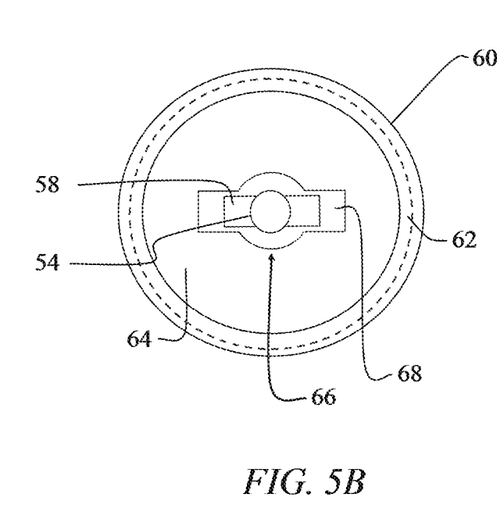
FIG. 5B is a diagrammatic, end elevation view of a ratchet lock and release device wherein the piston and piston rod are rotated to disengage the ratchet plate, thereby allowing the inflation element to be retracted.

In an alternative embodiment, shown in FIGS. 5A and 5B retraction of piston 52 and hence deflation of balloon 20 is achieved by rotating piston rod handle 56 (not shown) and hence piston rod 54 until said ratchets align with said elongate opening. Said ratchets may then be withdrawn through said elongate opening in a leading-to-trailing direction. A ratchet lock design that relies on rotation of the rod and piston assembly eliminates the use of a movable ratchet plate and therefore improves the operational simplicity and reliability of the device. A multiple blade rod assembly with inset ratchet notches is also within the scope of this invention.

Also in a preferred embodiment, the volume of fluid reservoir 40 is adjusted at the time of manufacture with respect to the fluid volumes and pressures necessary to achieve predetermined radii of balloon 20 in its expanded state in order to accomplish progressive stricture dilation through controlled release of stricture wall tension. When the balloon is engaged in a stricture with a radius less than the radius of the maximally inflated balloon, wall tension is governed by the geometry of the stricture and not the geometry of the balloon, its elastic properties or its material composition.

Another feature of the invention, therefore, includes a plurality of markings, collectively denoted 20, imprinted upon or otherwise made a part of barrel 42. The markings of a preferred embodiment are transversely disposed relative to a longitudinal axis of device 10 and are longitudinally spaced apart from one another. Accordingly, device 10 is tuned such that volume transfer marks 20 directly correspond to increases in system pressure within balloon 20, in accordance with Pascal's principle, capable of producing controlled tension release within the stricture (stretching) and thus allowing controlled unit increase in stricture and balloon radius, in accordance with LaPlace's law without direct monitoring of system pressure or direct visualization of balloon 20.

Those who have worked with prior art balloon dilation systems will appreciate the absence of any need to assemble component parts and the other advantages that flow from the novel structure. Prior art devices, for example, are filled during the dilation procedure by personnel often unfamiliar with sufficient mechanical experience.

Another feature of device 10, therefore, is the fact that the novel trans-endoscopic self-contained hydraulic balloon dilation system is provided in the form of an integrated unit so that no assembly is required. The invention includes the elimination of the need for assembly as well the elimination of the need to adjust the volume of the hydraulic fluid relative to the balloon. The relation of the amount of fluid to the inflation of the balloon is necessary for the graduated markings to give an accurate representation of balloon inflation. The term 'integral' or 'integrated' is not limited to a fabrication of the parts from a single piece of material, but is inclusive of other means for maintaining the parts fixed together as a single unit.

Moreover, fluid reservoir 40 cannot be removed from shaft 30 because it is integrally formed with the shaft. More particularly, it is directly extruded from the fluid reservoir tube at the time of manufacture. The extruded material may be polyethylene or any other extrudable plastic. If a manufacturer chooses to forego extrusion and to permanently glue or weld the fluid reservoir to the shaft instead, such permanent attachment is performed at a factory and not in an operating room by untrained personnel. Fluid reservoir 40 is advantageously pre-filled at the time of manufacture with an appropriate non-toxic hydraulic fluid. The integrally formed, trans-endoscopic self-contained hydraulic balloon system thereby eliminates procedure delays incurred by component collection and assembly and operational errors incurred by device complexity and lack of operational training. Because this insight is contrary to the understanding, practices and expectations of the art, the structure effectuating it would not have been obvious to those skilled in the art when considered as a whole.

It will be seen that the advantages set forth above, and those made apparent from the foregoing description, are efficiently attained and since certain changes may be made in the above construction without departing from the scope of the invention, it is intended that all matters contained in the foregoing description or shown in the accompanying drawings shall be interpreted as illustrative and not in a limiting sense. It should be understood that the examples and embodiments described herein are for illustrative purposes only and that various modifications or changes in light thereof will be suggested to persons skilled in the art and are to be included within the spirit and purview of this application. All patents, patent applications, provisional applications and publications referred to or cited herein are incorporated by reference in their entirety, including all figures and tables, to the extent they are not inconsistent with the explicit teachings of this specification.

It is also to be understood that the following claims are intended to cover all of the generic and specific features of the invention herein described, and all statements of the scope of the invention which, as a matter of language, might be said to fall there between.

What is claimed is:

1. A method of dilating a stricture in a body conduit of a subject comprising:
   providing a trans-endoscopic hydraulic balloon dilation apparatus comprising:
   a balloon;
   a hydraulic fluid reservoir having a leading end and a trailing end;
   an elongate hollow shaft having a lumen in open fluid communication with the balloon at a first end and the hydraulic fluid reservoir at a second end, whereby fluid in the fluid reservoir may flow through the lumen of the shaft into the balloon to cause expansion of the balloon;
   a centrally apertured hub secured to a trailing end of the fluid reservoir;
   a piston, secured to the leading end of an elongate piston rod, slideably positioned within a lumen of the fluid reservoir, wherein a trailing end of the piston rod extends through the hub and is external to the fluid reservoir whereby displacement of the piston rod in a trailing-to-leading direction causes expansion of the balloon; and
   a retention mechanism positioned on the piston rod wherein the retention mechanism is comprised of:

a plurality of ratchet members having a flexible and resilient construction wherein the plurality of ratchet members are positioned longitudinally on the piston rod and wherein each ratchet member is narrow at its leading end and wide at its trailing end;

a disc-shaped ratchet plate disposed at a trailing end of the fluid reservoir;

an elongate opening formed in center of the disc-shaped ratchet plate wherein the elongate opening is in registration with a diameter of the ratchet plate;

the elongate opening having an enlarged central portion that accommodates the piston rod;

the elongate opening central portion having a width less than a breadth of the ratchet members;

the elongate opening having a length greater than the breadth of the ratchet members;

wherein the ratchet members are freely moveable through the elongate opening when the elongate opening is aligned with the ratchet members and moveable in only one direction when the elongate opening is not in alignment with the ratchet members;

wherein when the elongate opening is not in alignment with the ratchet members, the ratchet members may be momentarily compressed when pushed through the elongate opening central portion for movement in only one direction;

whereby the retention mechanism locks the piston in a preselected position within the lumen of the fluid reservoir when the elongate opening is not aligned with the plurality of ratchet members;

inserting the trans-endoscopic hydraulic balloon dilation apparatus into the body conduit of the subject;

expanding the balloon of the trans-endoscopic hydraulic balloon dilation apparatus by displacing the piston rod in a trailing to leading direction, wherein balloon expansion dilates the stricture of the body conduit allowing visualization of the body conduit;

deflating the balloon by displacing the piston rod in a leading to trailing direction;

removing the trans-endoscopic hydraulic balloon apparatus from the body conduit of the subject.

2. The method of claim 1, wherein the trans-endoscopic hydraulic balloon apparatus further comprises:

a ratchet plate handle formed integrally with the ratchet plate, the ratchet plate handle extending radially from the ratchet plate;

the ratchet plate handle having a first position of rotational adjustment when the ratchets are pushed through the central part of the elongate opening; and the ratchet plate handle having a second position of rotational adjustment when the ratchets are aligned with the elongate opening to enable leading-to-trailing travel of the ratchets;

the second position being about ninety degrees (90°) from the first position;

whereby movement between the first position and the second position occurs through rotation of the ratchet plate handle in a circumferential direction.

3. The method of claim 1, wherein the trans-endoscopic hydraulic balloon apparatus further comprises:

a piston rod handle formed integrally with and extending radially from the piston rod;

the piston rod handle having a first position of rotational adjustment when the ratchets are pushed through the central part of the elongate opening in a proximal-to-distal direction;

the piston rod handle having a second position of rotational adjustment when the ratchets are retracted through the elongate opening in a leading-to-trailing direction.

4. The method of claim 1, wherein the trans-endoscopic hydraulic balloon apparatus further comprises:

an annular recessed step formed in the hub;

wherein the ratchet plate has a thickness substantially equal to a depth of the annular recessed step so that an annular peripheral edge of the ratchet plate is supported by the annular recessed step.

5. The method of claim 1, wherein the fluid reservoir is substantially transparent and further comprises a plurality of transversely disposed, longitudinally spaced markings provided on the fluid reservoir to facilitate visual inspection of the piston relative to the markings.

6. The method of claim 5, wherein the movement of the piston relative to the markings corresponds to a predetermined volume of hydraulic fluid being expelled from, or drawn into, the fluid reservoir.

7. A method of dilating a stricture in a body conduit of a subject comprising:

providing a trans-endoscopic hydraulic balloon dilation apparatus comprising:

a balloon;

a hydraulic fluid reservoir having a leading end and a trailing end;

an elongate hollow shaft having a lumen in open fluid communication with the balloon at a first end and the hydraulic fluid reservoir at a second end, whereby fluid in the fluid reservoir may flow through the lumen of the shaft into the balloon to cause expansion of the balloon;

a centrally apertured hub secured to a trailing end of the fluid reservoir;

a piston, secured to the leading end of an elongate piston rod, slideably positioned within a lumen of the fluid reservoir, wherein a trailing end of the piston rod extends through the hub and is external to the fluid reservoir;

a plurality of transversely disposed, longitudinally spaced markings provided on the fluid reservoir to facilitate visual inspection of the piston relative to the markings;

the hydraulic fluid reservoir, shaft and hub forming jointly a single integral and gaplessly continuous piece;

whereby displacement of the piston rod in a trailing-to-leading direction causes expansion of the balloon;

a retention mechanism positioned on the piston rod wherein the retention mechanism comprises a plurality of ratchet members having a flexible and resilient construction wherein the plurality of ratchet members are positioned longitudinally on the piston rod and wherein each ratchet member is narrow at its leading end and wide at its trailing end;

a disc-shaped ratchet plate disposed at a trailing end of the fluid reservoir;

an elongate opening formed in center of the disc-shaped ratchet plate wherein the elongate opening is in registration with a diameter of the ratchet plate;

the elongate opening having an enlarged central portion that accommodates the piston rod;

the elongate opening central portion having a width less than a breadth of the ratchet members;

the elongate opening having a length greater than the breadth of the ratchet members:

wherein the ratchet members are freely moveable through the elongate opening when the elongate opening is aligned with the ratchet members and moveable in only one direction when the elongate opening is not in alignment with the ratchet members;

wherein when the elongate opening is not in alignment with the ratchet members, the ratchet members may be momentarily compressed when pushed through the elongate opening central portion for movement in only one direction;

whereby the retention mechanism locks the piston in a preselected position within the lumen of the fluid reservoir when the elongate opening is not aligned with the plurality of ratchet members;

inserting the trans-endoscopic hydraulic balloon dilation apparatus into the body conduit of the subject;

expanding the balloon of the trans-endoscopic hydraulic balloon dilation apparatus by displacing the piston rod in a trailing to leading direction, wherein balloon expansion dilates the stricture of the body conduit allowing visualization of the body conduit;

deflating the balloon by displacing the piston rod in a leading to trailing direction;

removing the trans-endoscopic hydraulic balloon apparatus from the body conduit of the subject.

8. The method of claim 7, wherein the shaft is extruded from the fluid reservoir at the time of manufacture.

9. The method of claim 7, wherein the trans-endoscopic hydraulic balloon apparatus further comprises:

a ratchet plate handle formed integrally with the ratchet plate, the ratchet plate handle extending radially from the ratchet plate;

the ratchet plate handle having a first position of rotational adjustment when the ratchets are pushed through the central part of the elongate opening; and the ratchet plate handle having a second position of rotational adjustment when the ratchets are aligned with the elongate opening to enable leading-to-trailing travel of the ratchets;

the second position being about ninety degrees (90°) from the first position;

whereby movement between the first position and the second position occurs through rotation of the ratchet plate handle in a circumferential direction.

10. The method of claim 7, wherein the trans-endoscopic hydraulic balloon apparatus further comprises:

a piston rod handle formed integrally with and extending radially from the piston rod;

the piston rod handle having a first position of rotational adjustment when the ratchets are pushed through the central part of the elongate opening in a proximal-to-distal direction;

the piston rod handle having a second position of rotational adjustment when the ratchets are retracted through the elongate opening in a leading-to-trailing direction.

11. The method of claim 10, wherein the trans-endoscopic hydraulic balloon apparatus further comprises:

an annular recessed step formed in the hub wherein the ratchet plate has a thickness substantially equal to a depth of the annular recessed step so that an annular peripheral edge of the ratchet plate is supported by the annular recessed step.

12. The method of claim 7, wherein the movement of the piston relative to the markings corresponds to a predetermined volume of hydraulic fluid being expelled from, or drawn into, the fluid reservoir.

\* \* \* \* \*